United States Patent [19]

Veronese et al.

[11] Patent Number: 5,286,637
[45] Date of Patent: Feb. 15, 1994

[54] BIOLOGICALLY ACTIVE DRUG POLYMER DERIVATIVES AND METHOD FOR PREPARING SAME

[75] Inventors: Francesco Veronese; Luciana Sartore, both of Padua, Italy; Piero Orsolini, Martigny; Romano Deghenghi, S.-Cergue, both of Switzerland

[73] Assignee: Debiopharm, S.A., Lausanne, Switzerland

[21] Appl. No.: 1,434

[22] PCT Filed: Jul. 26, 1990

[86] PCT No.: PCT/EP90/01261

§ 371 Date: Jun. 3, 1991

§ 102(e) Date: Jun. 3, 1991

[87] PCT Pub. No.: WO91/01758

PCT Pub. Date: Feb. 21, 1991

Related U.S. Application Data

[63] Continuation of Ser. No. 681,493, Jun. 3, 1991, abandoned.

[30] Foreign Application Priority Data

Aug. 7, 1989 [GB] United Kingdom ............... 891009.5
Aug. 30, 1989 [GB] United Kingdom ............ 8919618.2

[51] Int. Cl.$^5$ .................. C12N 9/00; C12P 21/06; A01N 37/18
[52] U.S. Cl. .................. 435/183; 435/68.1; 435/181; 435/189; 435/832; 514/2; 530/397; 530/399; 424/85.91; 424/94.4
[58] Field of Search ............. 435/183, 832, 189, 69, 435/181; 424/85.91, 94.4; 514/2; 530/397, 399

[56] References Cited

U.S. PATENT DOCUMENTS

| | | | |
|---|---|---|---|
| 4,179,337 | 12/1979 | Davis et al. ................. | 435/181 |
| 4,766,106 | 8/1988 | Katre et al. .................. | 514/2 |
| 4,791,192 | 12/1988 | Nakagawa et al. ............. | 530/397 |
| 4,894,443 | 1/1990 | Greenfield et al. ............. | 530/388 |
| 4,935,355 | 6/1990 | Ulmer et al. .................. | 435/832 |
| 5,066,591 | 11/1991 | Hallewell et al. .............. | 435/189 |

FOREIGN PATENT DOCUMENTS 1156217 11/1983 Canada .
0098110 1/1984 European Pat. Off. .

OTHER PUBLICATIONS

K. Ulbrich et al., Poly(ethylene glycols) Containing Enzymatically Degradable Bonds, Makromol. Chem. 187, 1131-1144 (1986.

F. Veronese, et al; "Applied Biochemistry & Biotechnology"; vol. (11), pp. 141-152; (1985) Surface Modification of Proteins (Activation of Monomethoxy-Polyethylene Glycols by Phenylchloroformates and Modification of Ribonuclease and Superoxide Dimutase).

Savoca et al; "Preparation of Non-Immunogenic Arginase by the Covalent Attachment of Polyethylene Glycol"; Biochimica et Biophysica Acta, 578 (1979)pp. 47-53.

Primary Examiner—Michael G. Wityshyn
Assistant Examiner—Louise N. Leary
Attorney, Agent, or Firm—Pennie & Edmonds

[57] ABSTRACT

New biologically active drug polymer derivatives, namely peptides or protein derivatives, are useful medicaments and are represented by the generic formula:

$$RO-(CH_2-CH_2O)_n-(CO)-NH-X-(CO)-NH-Z \quad (I)$$

wherein
R represents a lower alkyl group,
n is an integer comprised between 25 and 250,
X when combined with adjacent NH and CO groups represents an amino acid or a dipeptide or tripeptide residue, and
Z when combined with the adjacent NH group represents a biologically active peptide or protein or NH or $NH_2$ containing drug residue.

6 Claims, 3 Drawing Sheets

M-PEG-Trp-OH

H-Trp-OH

M-PEG-Phe-OH

H-Phe-OH

M-PEG-Trp-SOD

M-PEG-Gly-SOD

BIOLOGICALLY ACTIVE DRUG POLYMER DERIVATIVES AND METHOD FOR PREPARING SAME

This is a continuation of application Ser. No. 07/681,493, filed Jun. 3, 1991, now abandoned.

The invention relates to new biologically active drug polymer derivatives, namely, peptides or protein derivatives useful as medicaments. It relates more particularly to peptide or protein polyethylene glycol derivatives wherein the peptide or protein moeity is linked to the polyethylene glycol residue by means of an amino acid or peptide spacer arm.

Modification of biologically active substances such as peptides or proteins with monomethoxy polyethylene glycol is reported to change extensively their physical, chemical, enzymological, immunological, as well as their pharmacological and pharmacokinetic properties. Several methods to achieve such a modification have so far been reported (see e.g. U.S. Pat. Nos. 4,179,337 and 4,766,106; Appl. Biochem and Biotechnology, Vol. 11, p. 141/1985).

Such modified peptide or protein derivatives exhibit some advantages when compared to the peptide or protein itself: increased water solubility, decreased antigenicity or increased half-life of the circulating peptide or protein.

The use of such modified bioactive compounds, however, is not satisfying as the following drawbacks have been observed: difficulty to obtain a selective incorporation of a radioactive probe into the polymer drug adduct necessary for pharmacokinetic experiments; inactivation of some enzymes; difficulty to program (or to modulate) the cleavage of the polymer-protein bond by specific enzymes in the body; difficulty of introduction into the polymerdrugs adduct amino acid sequences which may confer targeting properties to the adducts itself. These disadvantages are related to the chemistry employed in the polymer activation and to its direct linkage to the drug.

It has been found that some, if not all of the above mentioned drawbacks can be eliminated or at least significantly reduced by making use of the new drug polymer derivatives of the invention which are represented by the generic formula

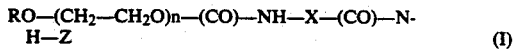

RO—(CH$_2$—CH$_2$O)n—(CO)—NH—X—(CO)—NH—Z  (I)

wherein
R represents a lower alkyl group,
n is an integer comprised between 25 and 250,
X when combined with adjacent NH and CO groups represents an amino acid or a dipeptide or tripeptide residue, and
Z when combined with the adjacent NH group represents a biologically active peptide or protein or NH or NH$_2$-containing drug residue.

Preferred species of compounds of formula (I) are those wherein R represents a methyl group and wherein n is an integer comprised between 40 and 115, i.e. those of which the polyethylene moiety exhibits a molecular weight of about 1800 to 5500, for example of 1900 and 5000.

Also preferred are the compounds of formula (I) wherein symbol X when combined with the adjacent NH and CO groups represents an amino acid selected from glycine, phenylylanine, tryptophan and norleucine, or a dipeptide or tripeptide such as Gly-Gly, Arg-Arg, Phe-Arg, Gly-Gly-Arg, Gly-Gly-Phe or Gly-Leu-Gly-Leu.

Also preferred are the compounds of formula (I) wherein symbol Z, when combined with the adjacent NH group represents the residue of a biologically active peptide, protein or drug, selected from the following species:
enzymes such as superoxidedismutase, ribonuclease, arginase, asparaginase, urokinase, e.g.;
antibiotics such as ampicillin, doxorubicin e.g.;
synthetic drugs like N-desmethyl-tamoxifen;
peptides such as LHRH and synthetic analogues of same, somatostatin and synthetic analogues of same, e.g.;
proteins such as interleukin-2, tumor necrosis factor, insulin, IGF-1 e.g.;
nucleosides such as adenin-arabinoside (ara-A), cytosin-arabinoside (ara-C), acyclovir e.g.

This enumeration is in no way limitative.

Some but not all of the most interesting peptide derivatives of formula (I) are mentioned and characterized individually in the Examples.

Consequently, the invention relates to new biologically active peptide derivatives of formula (I) as defined above, as well as to a method for preparing same.

The invention also relates to pharmaceutical compositions which comprise at least one of the compounds of formula (I) as active ingredient. Further objects of the invention shall appear from the specification or the claims.

The method of the invention is based on the linkage of an amino acid or peptide spacer arm of various structures and properties to the hydroxyl function of monoalkoxypolyethylene glycol through a carbonate linkage which involves the NH$_2$ group of the amino acid or peptide. This reaction is followed by the activation of the COOH function of the amino acid or peptide spacer arm as succinimidyl ester which, thus, becomes reactive towards the amino group of the biologically active peptide, protein or drug.

More specifically the method of the invention consists of:

a) reacting a mono-alkoxy-polyethylene glycol derivative of formula

RO—(CH$_2$—CH$_2$O)$_n$H  (II)

wherein R and n have the definition provided above, with 2,4,5-trichlorphenylchloroformate or 4-nitrophenylchloroformate to obtain the corresponding carbonate;

b) reacting the carbonate thus obtained with an amino acid or a di- or tripeptide of formula

H$_2$N—X—(CO)OH  (III)

wherein X is defined above to obtain a compound of formula

RO—(CH$_2$—CH$_2$O)$_n$—(CO)—NH—X—(CO)OH  (IV)

c) converting the compound of formula (IV) thus obtained into the corresponding succinimidyl ester, and d) finally, reacting the said succinimidyl ester with a biologically active peptide or protein or NH or NH$_2$-containing drug of formula

R—NH—Z or H₂N—Z    (V)

wherein R and Z are defined as indicated above. Steps a) through d) of the above described method do not necessitate special reaction conditions and can be carried out according to the usual techniques. Details of each of the above reaction steps are provided in the Examples illustrating the invention.

By means of the introduction of such a new spacer arm (amino acid or peptide) an improved targeting of the bioactive protein or drug is achieved: an enhanced lyposomal degradation of the peptide derivative of formula (I), a site-specific cleavage of the derivative by specific cellular enzymes as well as, in some instances, an increased binding of the derivative to specific cellular receptors which recognize the amino acid moiety.

There are still additional advantages: the new spacer arm may contain a residue which can be conveniently used to quantitate directly the polymer chains introduced into the protein. This can be performed by UV absorption in the case of tryptophan or phenylalanine, or by amino acid analysis in the case of norleucine which is not naturally present in proteins from natural sources.

The spacer arm may also be made radioactive using labelled amino acids, which simplifies to a great extent the detection of the biologically active peptide derivative during pharmacokinetic or metabolic experiments.

Some of these interesting properties are illustrated in the following Examples which are not limitative. In the said Examples the term "M-PEG" defines a monomethoxypolyethylene glycol and the amino acids or peptides are described by means of the terms usual in the art.

A. Preparation of activated M-PEG with an amino acid or peptide spacer arm

EXAMPLE 1

M-PEG 5000-Gly-Succinimidyl ester (M-PEG 5000-Gly-OSu)

To 10 g (2 mM) of M-PEG-5000, dissolved in 50 ml of anhydrous methylene chloride, 0.56 ml (4 mM) of triethylamine (TEA) and 0.81 g (4 mM) of 4-nitrophenyl chloroformate were added under stirring while the pH was adjusted at 7.5–8.0 with TEA. The reaction mixture was maintained at room temperature for 4 hrs. The mixture, concentrated under vacuum to about 10 ml, was dropped into 200 ml of stirred diethyl ether. The precipitate was collected by filtration and crystallized twice from hot ethyl acetate. The yield of M-PEG-p-nitrophe-nylcarbonate (M-PEG-OCO-OPh-NO₂), calculated spectrophotometrically on the basis of p-nitrophenol absorption was over 95%.

Glycine 1.5 g (20 mM) were dissolved in 20 ml of water, the solution was adjusted to pH 8.0–8.3 and added under stirring of 10.33 g (2 mM) of M-PEG-OCO-O-Ph-NO₂ while the pH was maintained at 8.3 with NaOH. After 4 hrs at room temperature the solution, cooled at 0° C. and brought to pH 3 with 2N HCl, was extracted three times with CHCl₃. The chloroform was washed with water, dried with Na₂SO₄, concentrated, precipitated with diethyl ether and the precipitate recrystalized from ethanol. The yield, calculated by COOH titration and glycine evaluation by conventional amino acid analysis after acid hydrolysis, was 85%.

M-PEG-Gly-OH 10.2 g (2 mM) was dissolved in 50 ml of anhydrous methylene chloride, cooled to 0° C., and 0.46 g (4 mM) of N-hydroxysuccinimide and 0.83 g (4 mM) of N,N-dicyclohexylcarbodiimide were added under stirring. The stirring was continued for 4 hrs, while the temperature was raised to 20° C. The precipitated dicyclohexylurea was removed from the reaction mixture by filtration, the solution was concentrated under vacuum and the product precipitated with diethyl ether and recrystallized from ethyl acetate. The yield of esterification, calculated from the UV hydroxysuccinimide absorption, was 85%.

Starting from M-PEG 1900 the M-PEG-1900-Gly-OSu derivative was obtained following the same procedure with a similar yield.

EXAMPLE 2

M-PEG 5000-Trp-succinimidyl ester (M-PEG 5000-Trp-OSu)

Figure 1:
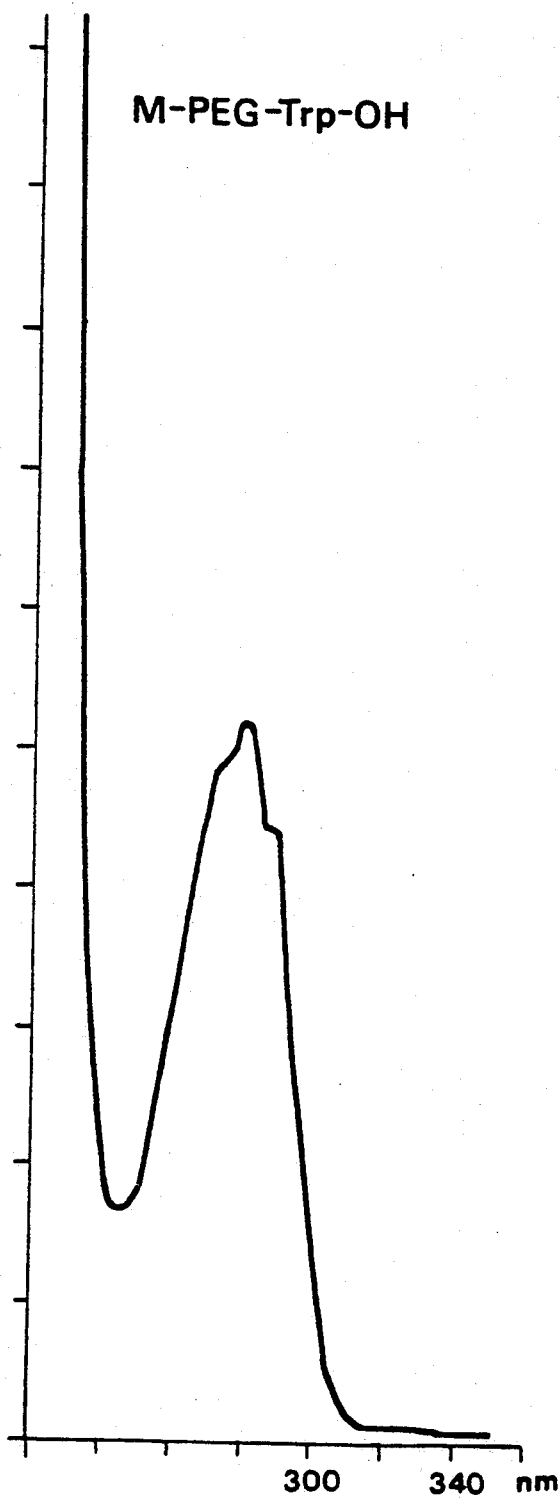
FIG. 1 illustrates a chromatograph of the amino acid tryptophan modified with monomethoxypolyethylene glycol (M-PEG).
Figure 1A:
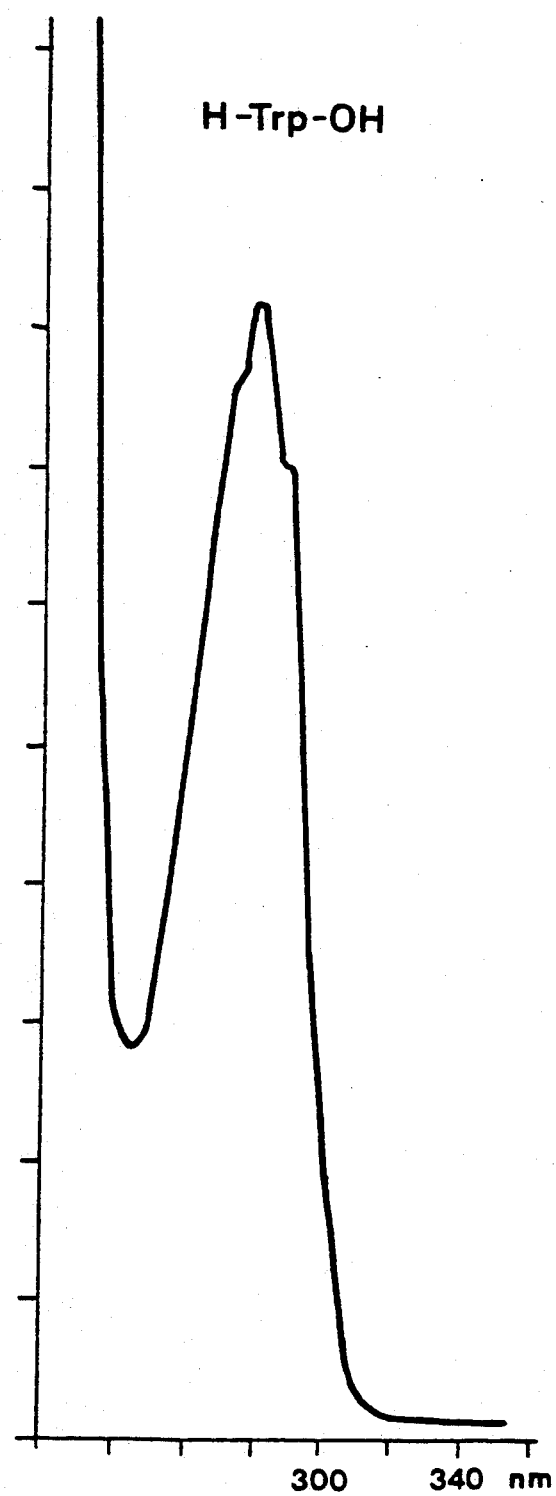
FIG. 1a illustrates a chromatograph of the amino acid tryptophan.

The procedure described above gave the PEG-tryptophan derivative with a yield of 80% calculated on the basis of the hydroxysuccinimide absorption as well as the tryptophan absorption at 280 nm (FIG. 1a).

The product presented the characteristic tryptophan absorption spectra as reported in FIG. 1.

EXAMPLE 3

M-PEG 5000-Phe-succinimidyl ester (M-PEG 5000-Phe-OSu)

Figure 2:
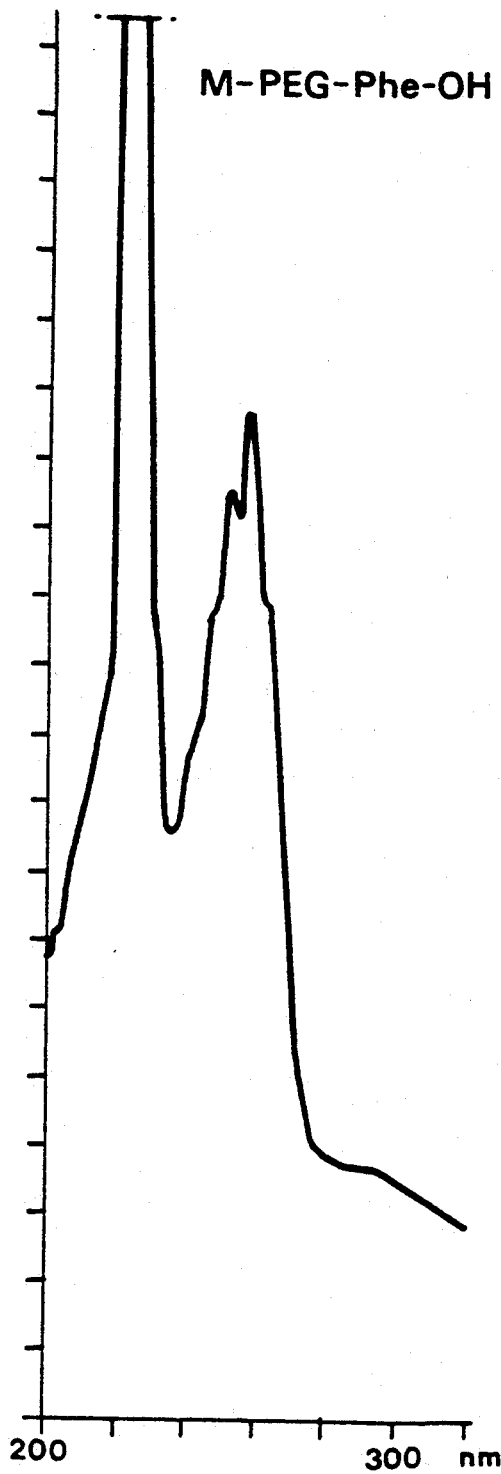
FIG. 2 illustrates a chromatograph of the amino acid phenalanine modified with monomethoxypolyethylene glycol (M-PEG).
Figure 2A:
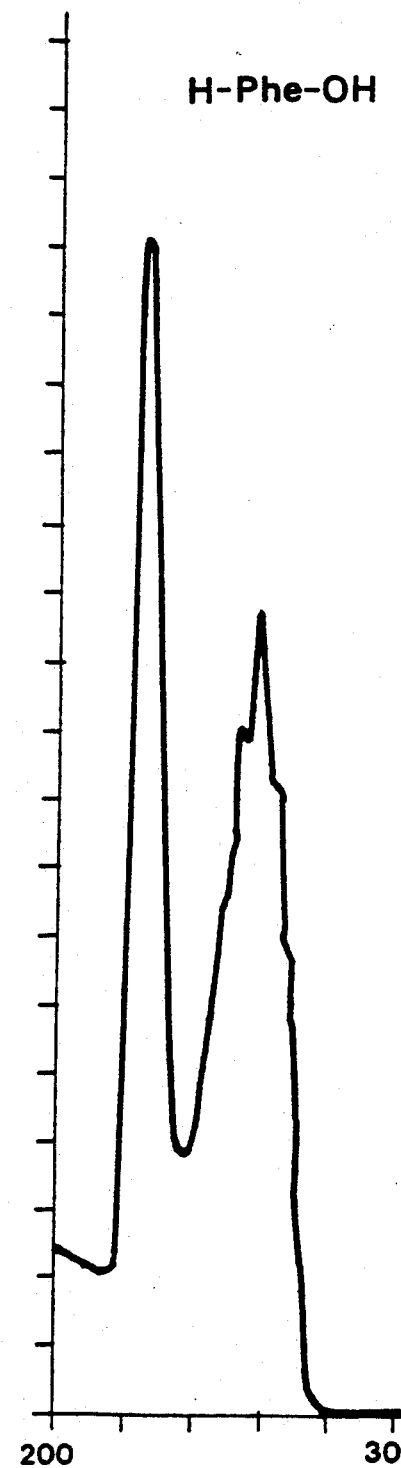
FIG. 2a illustrates a chromatograph of the amino acid phenalanine.

Following the procedure reported in Example 1 the M-PEG phenylalanine derivative was obtained. The product gave the spectra reported in FIG. 2 with the typical phenylalanine absorption at 260 nm (FIG. 2a).

EXAMPLE 4

M-PEG-nor-Leu-succinimidyl ester (M-PEG-5000-nor-Leu-OSu)

This derivative was obtained as above described with both M-PEG 5000 and M-PEG 1900. The 95% yield was calculated by nor-Leu evaluation on an amino acid analyzer after acid hydrolysis.

EXAMPLE 5

M-PEG 5000-Gly-Gly-succinimidyl ester (M-PEG-5000-Gly-Gly-OSu)

Using Gly-Gly as a model compound, the procedure already described under Example 1 was followed to prepare an activated monomethoxy polyethylene glycol with a dipeptide as a spacer arm. The product, crystallized from ethyl acetate, was obtained with a 85% yield.

B. Bioactive substances modification with amino acid derivatized M-PEG

EXAMPLE 6

Superoxide dismutase modification

6.1. With M-PEG 5000-Gly-OSu

Yeast superoxide dismutase (SOD, EC 1.15.1.1.) (100 mg) were dissolved in 10 ml of borate buffer 0.2 M pH 8 and 640 mg of M-PEG 5000-Gly-OSu were added at room temperature under vigorous stirring while the pH was maintained. The mixture was left standing for 30 min.

The extent of linked polymer chains, determined on the basis of amino groups modification evaluated according to the method of trinitrophenylation of Snyder and Sabocinski (Snyder S. I. and Sabocinsky P. Z., *Anal. Biochem,* 64 248–288, 1975) was over 85–90% while a 20% reduction in enzymatic activity was observed. The enzyme was evaluated by the method of Paoletti et al. (Paoletti F., Aldinicci D. Mocali A. and Caparrini A., *Anal. Biochem.,* 154 536–541, 1986).

The excess of polymer was removed by twice ultrafiltration on a PM 10 AMICON membrane and the concentrated enzyme chromatographied on a BIO-GEL A 0.5 m column. The M-PEG modified enzyme is eluted first as symetrical peak as revealed by UV absorption (FIG. 3a), iodine reaction for M-PEG and enzymatic activity. The excess of M-PEG is eluted later followed by the leaving group hydroxysuccinimide. The protein peak fractions are collected and lyophylized after membrane ultrafiltration. The M-PEG modified SOD is stored at 0° C. in a dessicator.

6.2- With M-PEG-5000-Trp-OSu

Figure 3:
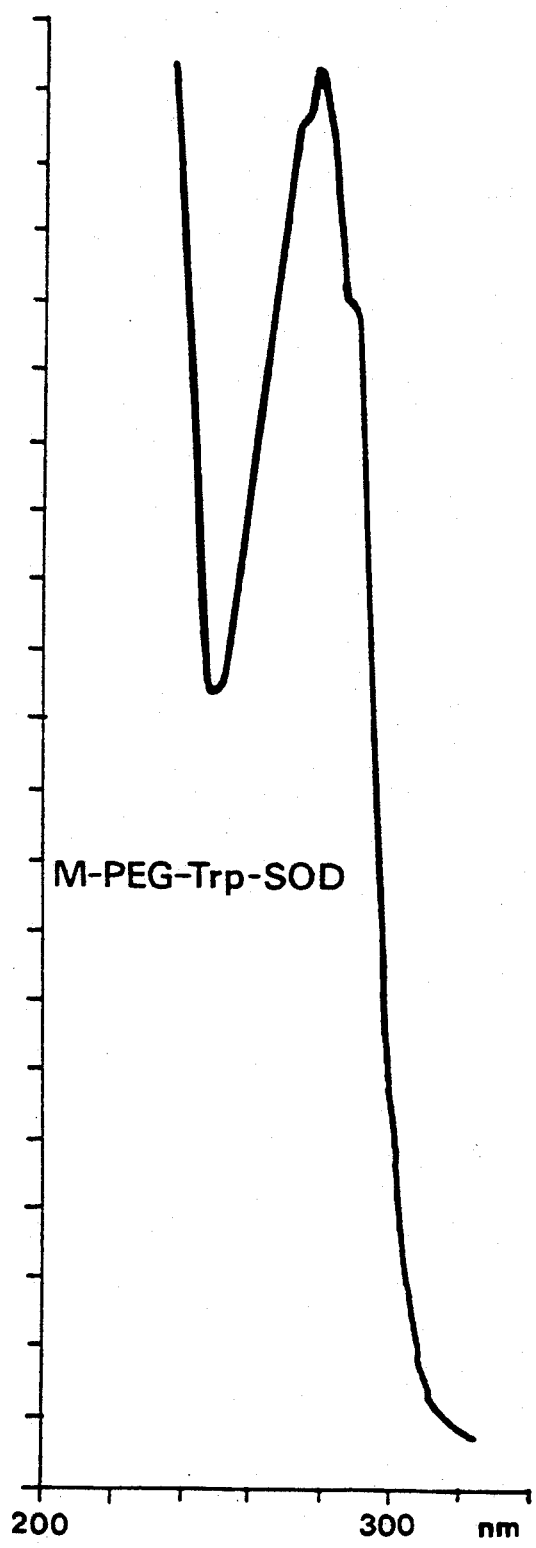
FIG. 3 illustrates a chromatograph of the amino acid tryptophan modified with M-PEG and superoxide dismutase (SOD).
Figure 3A:
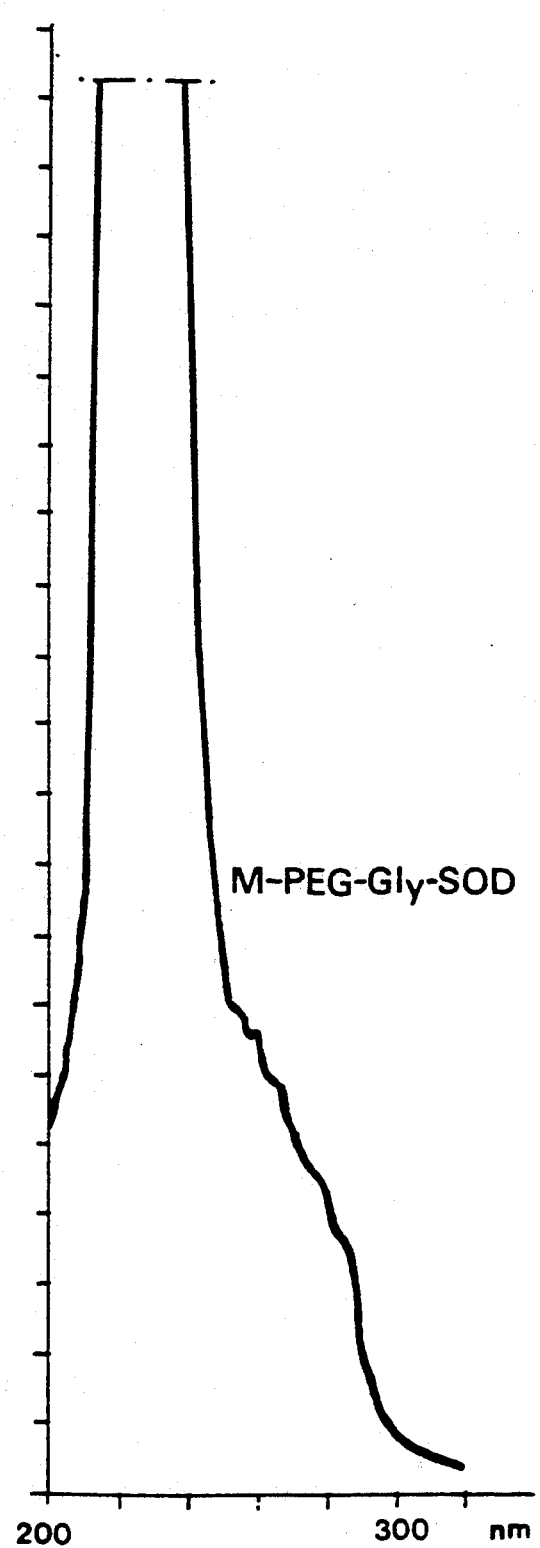
FIG. 3a illustrates a chromatograph of the amino acid glycine modified with M-PEG and superoxide dismutase (SOD).

The reaction was carried out as reported above (see 6.1); a similar extent of linked polymer chains to SOD and enzyme activity reduction was observed while the product presented the spectrum reported in FIG. 3 where the contribution of tryptophan is evident.

6.3- With M-PEG 5000-nor-Leu-OSu

The reaction carried out as reported in 6.1 gave a product with similar enzymatic properties and extent of modification by TNBS assay. In this case the amino acid analysis after acid hydrolysis revealed the presence of norleucine which accounted for 18 M-PEG chains bound to each SOD molecule in agreement with the TNBS test.

6.4- With M-PEG 1900-Gly-OSu

The reaction was carried out as in 6.1, similar results were obtained as far as polymer linkage and enzymatic activity is concerned, this product is eluted later from the column as expected from the lower molecular weight of the polymer used in the modification.

Comment to examples 6.1 through 6.4: the purification from unreacted M-PEG 5000 or M-PEG 1900 could be successfully reached by dilution of the reaction mixture (about 1 to 10 folds) followed by ultrafiltration concentration on an AMICON membrane; this procedure of dilution and ultrafiltration must be repeated at least 4 times.

Pharmacokinetic behavior of native and M-PEG-modified SOD

Unmodified yeast superoxide dismutase (5.5 mg) or equiactive amount of SOD modified with M-PEG 5000-Gly or M-PEG 1900-Gly were injected into the tail vein of Wistar albine male rats.

On a scheduled time the blood was removed by heart puncture with heparinized siringe and SOD evaluated in the plasma on the basis of its enzymatic activity. Before activity evaluation in plasma was purified from interferences by CM cellulose and SEPHADEX G 25 column chromatography. A 50 % clearance of 6 min, 15 and 28 hrs was respectively found for the native, the M-PEG 1900 and M-PEG 50000 modified derivatives.

Enzymatic properties

The stability of the M-PEG 1900 and M-PEG 5000 modified yeast superoxide dismutase to different conditions are as follows:

a. The M-PEG modified enzyme is less stable to incubation in a protein denaturant such 2M guanidinium chloride; after 4 hrs its residual activity is 10% in comparison to the 20% of the native enzyme.

b. The M-PEG 5000-Gly-SOD was maintained in water at a concentration of 1 mgml at 0°, 20° or 35° C. No loss of activity was found for at least 8 days incubation. The stability was also observed after 8 days standing at 20° C. at a concentration as low as 0.01 mg/ml.

The M-PEG 5000-Gly-SOD was found to be stable to repeated freezing and thawing cycles.

A M-PEG enzyme solution was evaporated to dryness at low temperature under vacuum, dissolved and again concentrated; the M-PEG modified enzyme was stable for at least six of such cycles while the unmodified enzyme lost at least 15% of its activity under the same conditions.

The M-PEG 5000-Gly-SOD was completely stable to repeated cycles of dissolution and lyophilization whereas the free enzyme at each treatment lost about 5% of its activity.

The M-PEG 5000-Gly-SOD, in the presence of metal chelates, was found to lose with greater difficulty the metals essential for the activity as compared to the free enzyme.

EXAMPLE 7

Arginase modification (M-PEG 5000-Gly-arginase

Bovine liver arginase (EC 3.5.3.1), 100 mg, highly purified according to literature to give a specific activity of 1900 IU/mg, was dissolved in 15 ml of carbonate buffer pH 8.5, 0.2M and 800 mg of M-PEG 5000-Gly-OSu were added under vigorous stirring while the pH was maintained by a pH-stat with NaOH 0.1N in a microburette. After 30 minutes the solution was diluted to 50 ml with water and ultrafiltered at 4° C. with an AMICON PM 10 ultrafiltration membrane to reduce the volume to about 5 ml. The M-PEG modified arginase was purified from excess reagent and by-products of reaction through column chromatography as reported in Example 1. The binding of polymer was at the level of over 50% of arginase amino groups while only a 5% reduction in arginase activity was detected.

Enzymatic and pharmacokinetic properties of M-PEG-5000-Gly-arginase

The modification increased the stability of the enzyme to the action of proteolyctic enzymes such trypsin, chimotrypsin, elastase and subtilysin.

The pharmacokinetic behavior of native and PEG derivatized enzyme was evaluated in the rats as reported under example 6.1. A 50% clearance time of 1.5 and 8 hrs was respectively found for the unmodified and the polymer modified arginase.

EXAMPLE 8

Ribonuclease modification (M-PEG 5000-Gly-ribonuclease)

Ribonuclease A (EC 2.7.7.16) from bovine pancreas was modified and purified as in example 6.1. The amount of M-PEG-Gly-OSu used for the modification was at a molar ratio of 2.5:1 calculated on the available amino groups of the enzymes. The modification resulted in the covalent linkage of 11 molecules of polymer for ribonuclease molecule.

The modification is accompanied by an enzyme activity loss of about 10% as verified with cytidine-2′,3′-cycle phosphate while the modified enzyme was found to be 50% active towards ribonucleic acid.

EXAMPLE 9

Urokinase modification (M-PEG-500-Gly-urokinase)

Urokinase (EC 3.4.4.a) from urine was modified and purified as reported under example 6.1. With this enzyme the modification was carried out using a molar ratio of activated polymer/protein amino group of 1:2. Under these circumstances about 10 molecules of polymer were linked to each urokinase molecule. The enzymatic activity evaluated on the lysis of thrombus was 30% of that of the native enzyme while its esterolitic activity, assayed on the synthetic substrate carbobenzoxy-lysine-O-nitrophenyl ester, was the same of the unmodified urokinase.

EXAMPLE 10

Ampicillin modification

10.1 - M-PEG 5000-Gly-Ampicillin

To a solution of ampicillin sodium salt, 50 mg (0,135 mM) in 5 ml of borate buffer 0,2M pH 8, 600 mg (0,12 mM) of M-PEG 5000-Gly-OSu were added under vigorous stirring.

The reaction mixture was left standing for 20 min, then separated by excess of ampicillin and of side products of reaction by gel filtration chromatography on a BIO GEL P 60 100–200 mesh column. The M-PEG modified drug was eluted first as a symmetric peak as revealed the UV absorption of ampicillin and the iodine reaction for PEG.

The drug modified peak fractions were collected, concentrated by ultrafiltration and lyophilized. The product was crystallized from ethyl acetate with a 70% yield based on the starting ampicillin. The same product was also prepared by the procedure that is reported below.

10.2 - M-PEG 5000-Gly-Ampicillin

Ampicillin sodium salt 100 mg (0.27 mM) were solved in 20 ml of N,N-dimethylformamide (DMF); 1.0 g (0.2 mM) of M-PEG 5000-Gly-OSu and 0.03 ml of 4-methylmorpholine (NMM) were added while pH was adjusted at 8–8.3 with NMM. The reaction mixture was maintained at room temperature under stirring for about 4 hrs and then concentrated to dryness under high vacuum. The residue was solved in 5 ml of $CH_2Cl_2$ which were dropped in stirred diethyl ether (100 ml). The precipitate was removed by filtration and crystallized.

The first crystallization was from hot ethyl acetate and the second one from hot methanol. The yield, based on the starting ampicillin, was 60%.

EXAMPLE 11

Doxorubicin modification (M-PEG 5000-Gly-doxorubicin)

To a solution of doxorubicin hydrocloride, 50 mg $(8.6.10^{-2} mM)$ of M-PEG 5000-Gly-OSu were added in portions. The mixture was left standing at room temperature under vigorous stirring; after 15 min the pH was adjusted at 7 with HCl 1M and the product purified from free drug and the leaving group hydroxysuccinimid by gel filtration chromatography on a BIO GEL P 60 100–200 mesh column. The M-modified drug was eluted as a peak with the typical UV absorption of doxorubicine (OD 230 and 480 nm) and the expected iodine reaction for MPEG. The M-PEG 5000-Gly-doxorubicin fractions were collected, concentrated by ultrafiltration and lyophilized. The product was further purified by chromatography on a BIO GEL A 0.5 m column. The overall yield, based on the starting drug, was 50%.

We claim:

1. Biologically active drug polymer derivatives having the formula

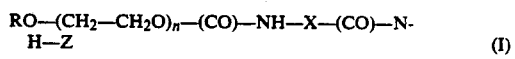
(I)

wherein
- R represents a lower alkyl group,
- n is an integer between 25 and 250,
- X when combined with adjacent NH and CO groups represents an amino acid or a dipeptide or tripeptide residue, and
- Z when combined with the adjacent NH group represents a biologically active peptide or protein or NH or $NH_2$ containing drug residue.

2. Drug polymer derivatives according to claim 1 wherein
- R represents a methyl group,
- n is an integer between 40 and 115,
- X when combined with adjacent NH and CO groups represents an amino acid residue selected from the group consisting of glycine, phenylanaline, tryptophan and norleucine, or a dipeptide or tripeptide residue selected from Gly-Gly, Arg-Arg, Phe-Arg, Gly-Gly-Arg, Gly-Gly-Phe, and Gly-Leu-Gly-Leu, and
- Z when combined with the adjacent NH group represents the residue of a biologically active peptide, protein or drug selected from the group consisting of superoxidedismutase, ribonuclease, arginase, asparaginase, urokinase, ampicilline, doxorubicine, N-desmethyl-tamixofen, LHRH and synthetic analogues of same, somatostatin and synthetic analogues of same, calcitonin, interleukin-2, tumor necrosis factor, insulin, IGF-1, natural or recombinant interferon, adenin-arabinoside (ara-A), cytosin-arabinoside (ara-C) and acyclovir.

3. Method for preparing biologically active drug polymer derivatives having the formula (I) as defined in claim 1 which comprises:

a) reacting a mono-alkoxy-polyethylene glycol derivative of formula $$RO-(CH_2-CH_2O)_nH \quad (II)$$

wherein R and n have the definition as indicated in claim 1 with 2,4,5-trichlorphenylchloroformate or 4-nitrophenylchloroformate to obtain the corresponding carbonate;

b) reacting the carbonate thus obtained with an amino acid or a di- or tripeptide of formula $$H_2N-X-(CO)OH \quad (III)$$

wherein X is defined as indicated in claim 1 to obtain a compound of formula $$RO-(CH_2-CH_2O)_n-(CO)-NH-X-(CO)OH \quad (IV)$$

such that the carbonate is bonded directly to the amino group ($-NH_2$) of the amino acid or peptide;

c) converting the compound of formula (IV) thus obtained into the corresponding succinimidyl ester; and d) finally, reacting the said succinimidyl ester with a biologically active peptide or protein or NH or $NH_2$-containing drug of formula $$R-NH-Z \text{ or } H_2N-Z \quad (V)$$

wherein R and Z are defined as indicated in claim 1 such that the peptide, protein or drug is bonded to the activated carboxyl function of the ester.

4. Pharmaceutical composition which comprises as an active ingredient at least one biologically active drug polymer derivative of formula (I) as defined in claim 1; and a pharmaceutically acceptable carrier.

5. Pharmaceutical composition according to claim 4 which comprises as active ingredient a biologically active drug polymer derivative of formula (I) wherein
R represents a methyl group,
n represents an integer between 40 and 115,
X when combined with adjacent NH and CO groups represents an amino acid residue selected from the group consisting of glycine, phenylanaline, tryptophan and norleucine, a dipeptide or tripeptide residue selected from Gly-Gly, Arg-Arg, Phe-Arg, Gly-Gly-Arg Gly-Gly-Phe and Gly-Leu-Gly-Leu, and
Z when combined with the adjacent NH group represents a biologically active peptide, protein or drug residue selected from the group consisting of superoxidedismutase, ribonuclease, arginase, asparaginase, urokinase, ampicilline, doxorubicine, N-desmethyl-tamoxifen, LHRH and synthetic analogues of same, somatostatin and synthetic analogues of same, calcitonin, interleukin-2, tumor necrosis factor, insulin, IGF-1 natural or recombinant interferon, adenin-arabinoside (ara-A), cytosin-arabinoside (ara-C) and acyclovir.

6. Pharmaceutical composition according to claim 5 which comprises as active ingredient a biologically active drug polymer derivative selected from the group consisting of
M-PEG 5000-Gly-superoxidedismutase,
M-PEG 5000-Trp-superoxidedismutase,
M-PEG 5000-nor-Leu-superoxidedismutase
M-PEG 1900-Gly-superoxidedismutase,
M-PEG 5000-Gly-arginase,
M-PEG 5000-Gly-ribonuclease,
M-PEG 5000-Gly-urokinase,
M-PEG 5000-Gly-ampicillin, and
M-PEG 5000-Gly-doxorubicin
wherein M-PEG represents monomethoxy-polyethylene.

* * * * *